United States Patent
Walker et al.

(10) Patent No.: US 10,653,583 B1
(45) Date of Patent: May 19, 2020

(54) PROGRAMMABLE PILL BOX ASSEMBLY

(71) Applicants: Gary Walker, Enola, PA (US); Samuel Steigerwalt, Enola, PA (US)

(72) Inventors: Gary Walker, Enola, PA (US); Samuel Steigerwalt, Enola, PA (US)

( * ) Notice: Subject to any disclaimer, the term of this patent is extended or adjusted under 35 U.S.C. 154(b) by 0 days.

(21) Appl. No.: 16/274,876

(22) Filed: Feb. 13, 2019

(51) Int. Cl.
  *G08B 1/00* (2006.01)
  *A61J 7/04* (2006.01)
  *A61J 7/00* (2006.01)
  *G16H 20/10* (2018.01)

(52) U.S. Cl.
  CPC ........... *A61J 7/0418* (2015.05); *A61J 7/0076* (2013.01); *A61J 7/0427* (2015.05); *A61J 7/0481* (2013.01); *G16H 20/10* (2018.01)

(58) Field of Classification Search
  CPC ...... A61J 7/0418; A61J 7/0427; A61J 7/0076; A61J 7/0481; G16H 20/10
  See application file for complete search history.

(56) References Cited

U.S. PATENT DOCUMENTS

| | | | |
|---|---|---|---|
| 4,126,224 A * | 11/1978 | Laauwe | B65D 50/06 206/540 |
| 5,646,912 A | 7/1997 | Cousin | |
| 5,752,235 A | 5/1998 | Kehr | |
| 5,850,937 A | 12/1998 | Rauche | |
| D422,713 S | 4/2000 | Lee | |
| 7,317,803 B1 | 1/2008 | Prabhakar | |
| 8,552,868 B1 | 10/2013 | Ferguson | |
| 9,161,885 B1 * | 10/2015 | Zhou | A61J 7/0418 |
| 9,218,458 B2 * | 12/2015 | Baarman | G06Q 10/087 |
| 9,770,390 B2 | 9/2017 | Aggarwal | |
| 9,901,516 B2 * | 2/2018 | Rodriguez | G16H 20/13 |
| 9,934,365 B2 * | 4/2018 | Turnell | A61J 7/0418 |
| 10,360,751 B2 * | 7/2019 | Berg | G06Q 10/087 |
| 2006/0180600 A1 | 8/2006 | Taylor | |
| 2009/0294521 A1 * | 12/2009 | de la Huerga | A61J 1/035 235/375 |
| 2009/0315702 A1 * | 12/2009 | Cohen Alloro | G16H 20/13 340/539.1 |
| 2013/0195326 A1 * | 8/2013 | Bear | G06F 19/3456 382/128 |
| 2014/0225491 A1 * | 8/2014 | Shoenfeld | A47B 81/00 312/237 |
| 2014/0309772 A1 | 10/2014 | Shen | |

(Continued)

FOREIGN PATENT DOCUMENTS

WO  WO2015091040  6/2015

*Primary Examiner* — Zhen Y Wu

(57) ABSTRACT

A programmable pill box assembly includes a pill box that has a plurality of compartments therein for containing pills. A plurality of doors is each hingedly coupled to the pill box. Each of the doors is aligned with a respective one of the compartments for opening and closing the compartments. A sensing unit is coupled to the pill box to sense when each of the doors is opened or closed. A transmission unit is removably coupled to the pill box and the transmission unit transmits an alert signal when the sensing unit senses that a respective one of the doors has not been opened at a predetermined time. A bracelet is worn on a wrist of the user and the bracelet is in wireless communication with the transmission unit. The bracelet vibrates to remind the user to take the pills in one of the compartments in the pill box.

10 Claims, 4 Drawing Sheets

(56) References Cited

U.S. PATENT DOCUMENTS

| | | | | |
|---|---|---|---|---|
| 2014/0350720 A1* | 11/2014 | Lehmann | ............ | G06F 19/3462 |
| | | | | 700/236 |
| 2015/0048102 A1* | 2/2015 | Dickie | ...................... | A61J 1/03 |
| | | | | 221/2 |
| 2015/0179032 A1* | 6/2015 | Johnson | ................. | G08B 21/24 |
| | | | | 340/541 |
| 2015/0283036 A1* | 10/2015 | Aggarwal | ................. | A61J 7/04 |
| | | | | 206/534 |
| 2016/0015602 A1* | 1/2016 | Panzini | ................. | A61J 7/0454 |
| | | | | 340/666 |
| 2017/0046501 A1* | 2/2017 | Coleman | .................. | A61J 1/035 |
| 2017/0087059 A1* | 3/2017 | Rodriguez | ............ | G16H 20/13 |
| 2017/0193189 A1* | 7/2017 | Turnell | ................. | A61J 7/0418 |
| 2017/0326034 A1* | 11/2017 | Lewis | .................... | A61J 7/0084 |
| 2018/0000692 A1* | 1/2018 | Born | ..................... | A61J 7/0481 |

* cited by examiner

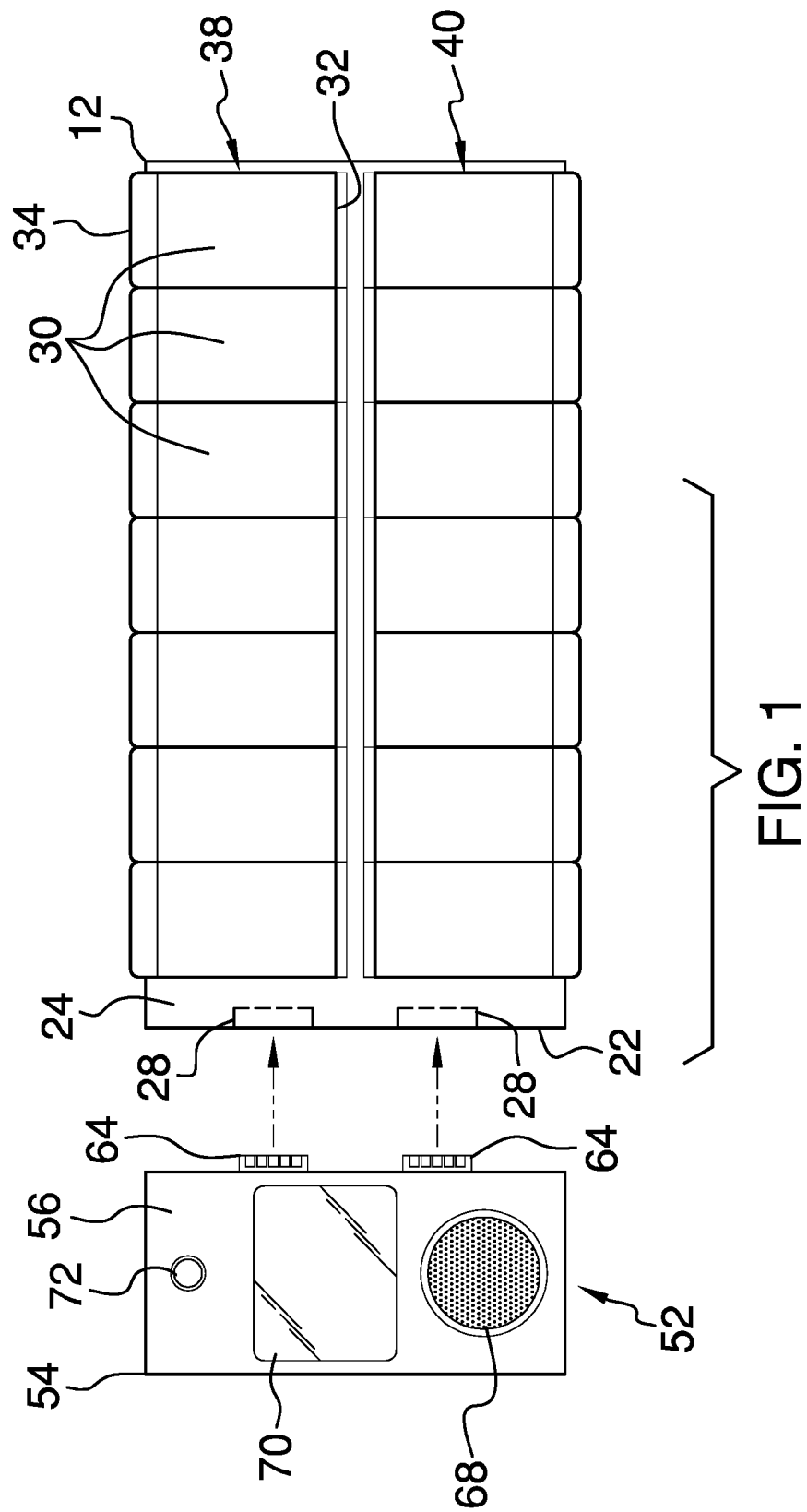

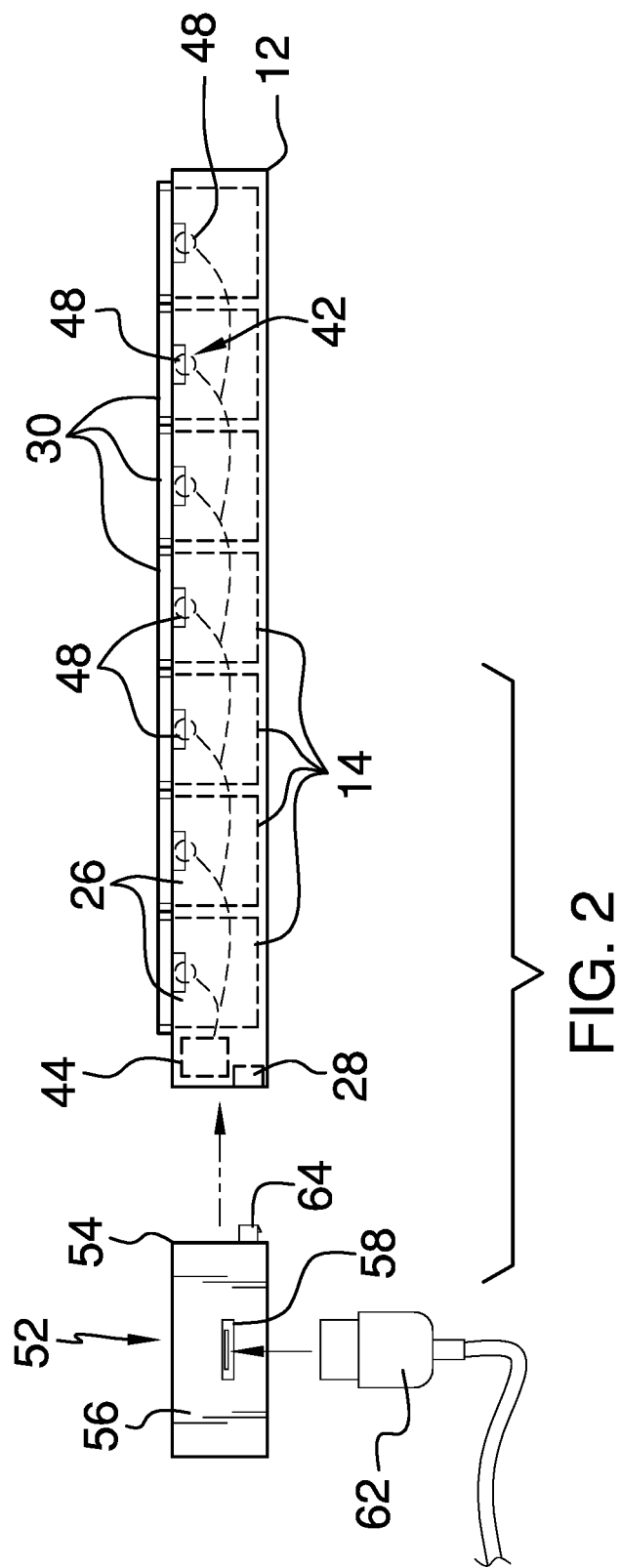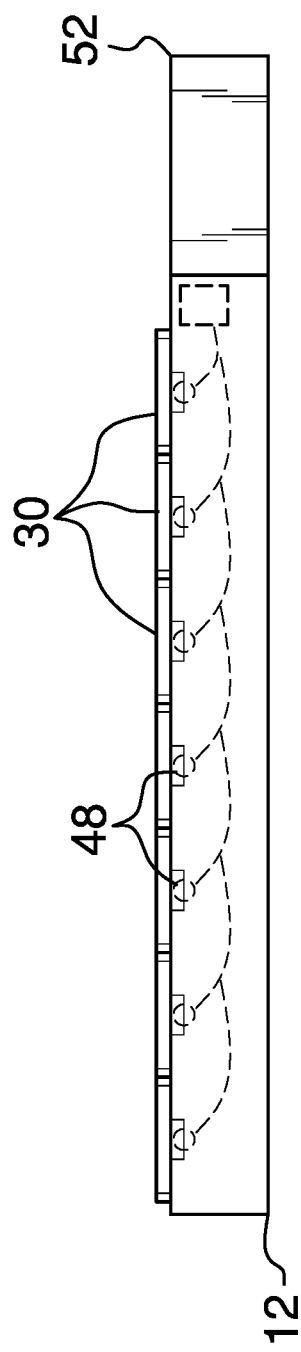

PROGRAMMABLE PILL BOX ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to pill box devices and more particularly pertains to a new pill box device for audibly, visually and physically reminding a user to take medication at a predetermined time.

BRIEF SUMMARY OF THE INVENTION

An embodiment of the disclosure meets the needs presented above by generally comprising a pill box that has a plurality of compartments therein for containing pills. A plurality of doors is each hingedly coupled to the pill box. Each of the doors is aligned with a respective one of the compartments for opening and closing the compartments. A sensing unit is coupled to the pill box to sense when each of the doors is opened or closed. A transmission unit is removably coupled to the pill box and the transmission unit transmits an alert signal when the sensing unit senses that a respective one of the doors has not been opened at a predetermined time. A bracelet is worn on a wrist of the user and the bracelet is in wireless communication with the transmission unit. The bracelet vibrates to remind the user to take the pills in one of the compartments in the pill box.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 1 is a top exploded view of a programmable pill box assembly according to an embodiment of the disclosure.

FIG. 2 is a front phantom view of an embodiment of the disclosure.

FIG. 3 is a back phantom view of an embodiment of the disclosure.

DETAILED DESCRIPTION OF THE INVENTION

Figure 4:
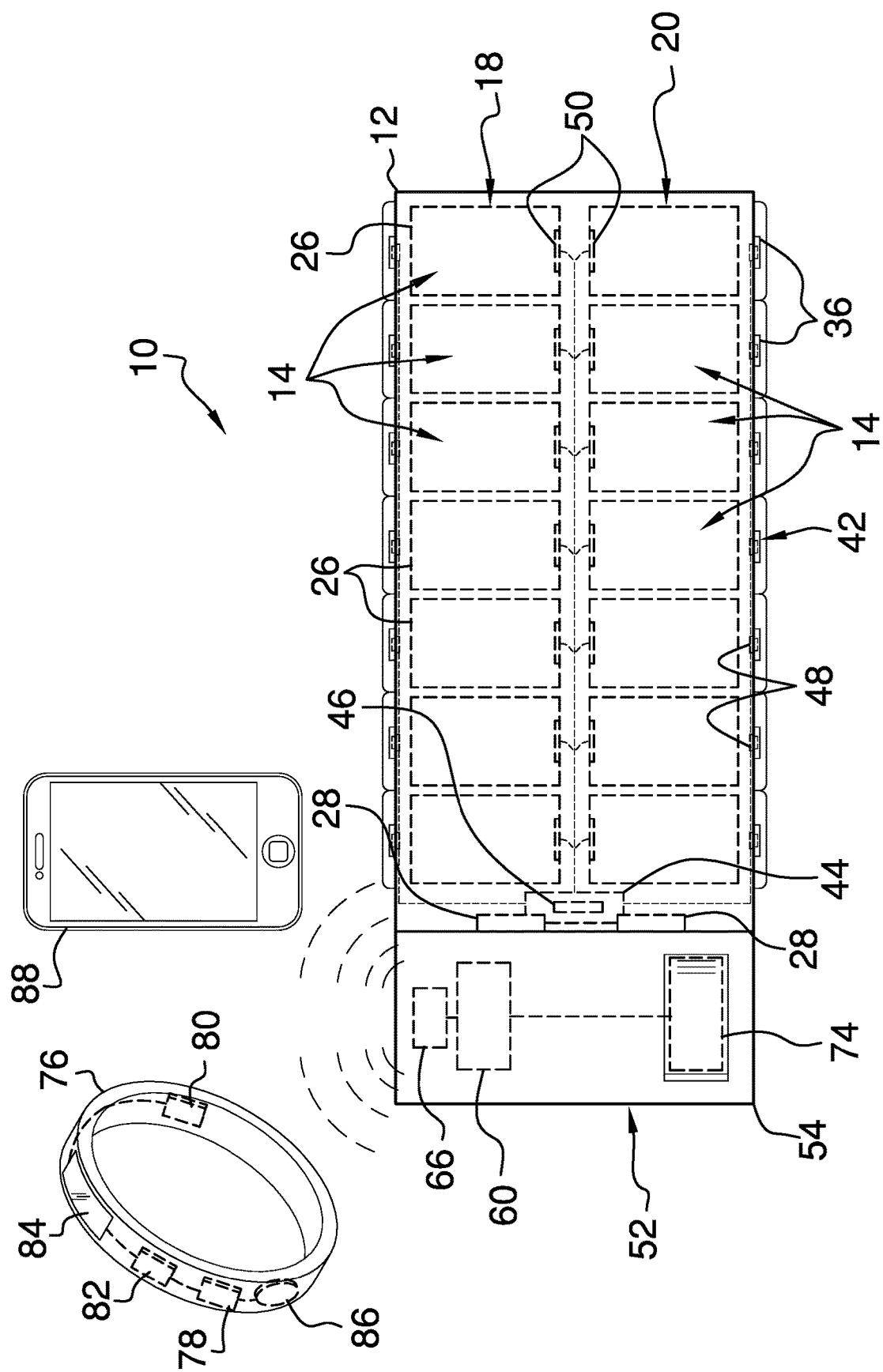
FIG. 4 is a top phantom view of an embodiment of the disclosure.
Figure 5:
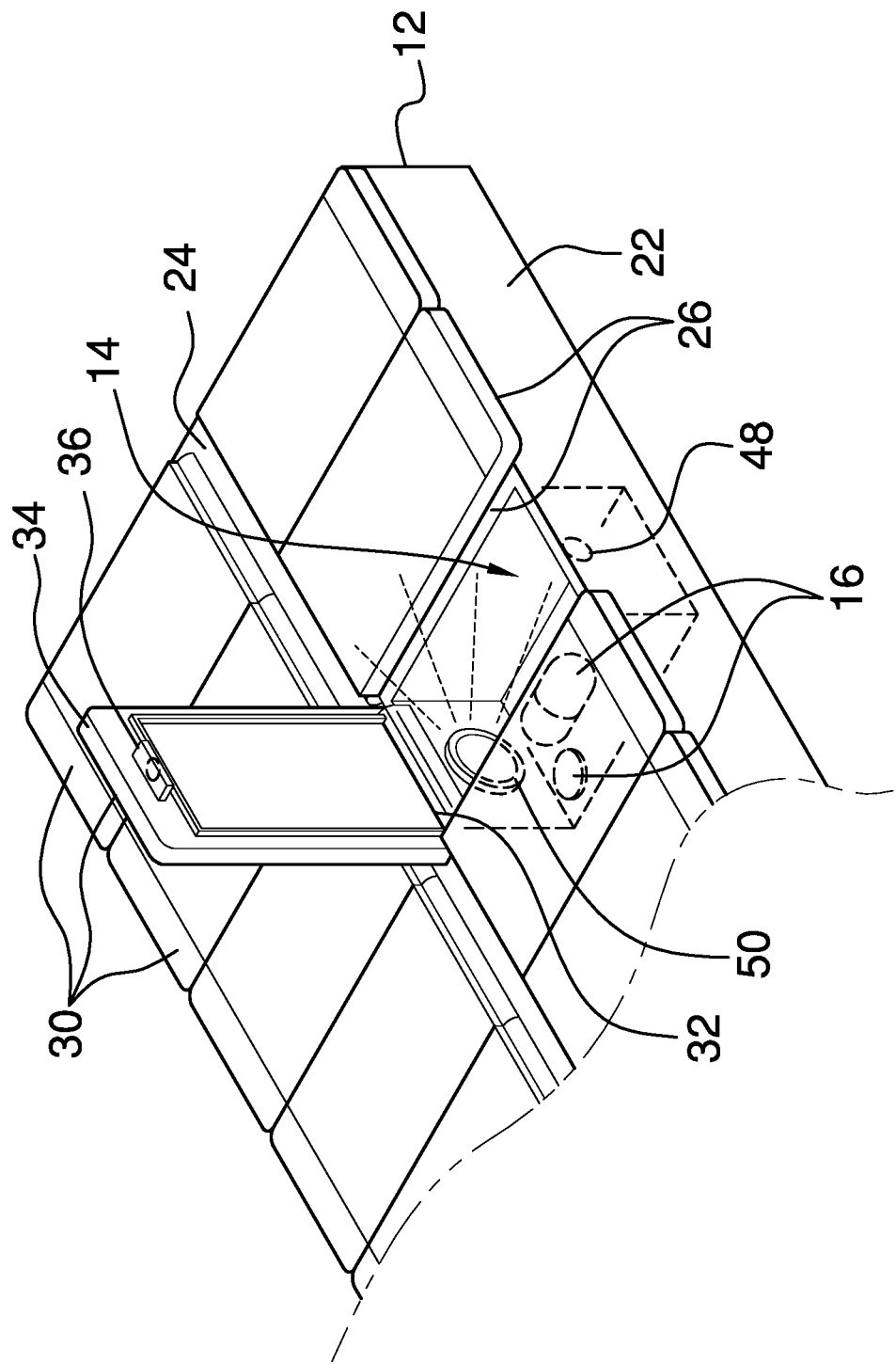
FIG. 5 is a perspective view of a door and a compartment of an embodiment of the disclosure.

With reference now to the drawings, and in particular to FIGS. 1 through 5 thereof, a new pill box device embodying the principles and concepts of an embodiment of the disclosure and generally designated by the reference numeral 10 will be described.

As best illustrated in FIGS. 1 through 5, the programmable pill box assembly 10 generally comprises a pill box 12 that has a plurality of compartments 14 therein. Each of the compartments 14 may have pills 16 positioned therein according to a prescription or the like. The plurality of compartments 14 includes a first bank of compartments 18 and a second bank of compartments 20. The pill box 12 has a perimeter wall 22 and a top wall 24, and the top wall 24 has a plurality of openings 26 each being aligned with a respective one of the first 18 and second 20 banks of compartments. Additionally, the perimeter wall 22 has a pair of data ports 28 extending inwardly therein. The data ports 28 may be electronic data ports of any conventional design.

A plurality of doors 30 is each of the doors 30 is hingedly coupled to the pill box 12. Each of the doors 30 is aligned with a respective one of the first 18 and second 20 banks of compartments for opening and closing the respective first 18 and second 20 banks of compartments. Each of the doors 30 has a back edge 32 and a front edge 34, and the back edge 32 of each of the doors 30 is hingedly coupled to the top wall 24 of the pill box 12. Each of the doors 30 has a tab 36 extending downwardly therefrom and the tab 36 on each of the doors 30 is aligned with the front edge 34 of the doors 30. Moreover, the tab 36 on each of the doors 30 is comprised of an electrically conductive or ferromagnetic material.

The plurality of doors 30 includes a set of first doors 38 that is each aligned with a respective one of the first bank of compartments 18. Additionally, the plurality of doors 30 includes a set of second doors 40 each that is each aligned with a respective one of the second bank of compartments 20. The back edge 32 of each of the set of first 38 and second 40 doors is directed toward a center of the pill box 12.

A sensing unit 42 is coupled to the pill box 12 and the sensing unit 42 is in operational communication with each of the doors 30. Moreover, the sensing unit 42 senses when each of the doors 30 is opened or closed. The sensing unit 42 comprises a pill box control circuit 44 that is coupled to the pill box 12. The pill box control circuit 44 receives an open input and a closed input. Additionally, the pill box control circuit 44 includes an electronic memory 46. The electronic memory 46 stores a database comprising a unique identity assigned to each of the compartments 14 in the pill box 12. The database further comprises a predetermined schedule for taking the pills 16 in each of the compartments 14. The electronic memory 46 may additionally store data pertaining to spoken words or phrases, such as a pre-recorded verbal reminder to take the pills 16.

The sensing unit 42 includes a plurality of sensors 48 that is each coupled to the pill box 12. Each of the sensors 48 is positioned in a respective one of the compartments 14 and each of the sensors 48 is electrically coupled to the pill box control circuit 44. The unique identity assigned to each of the compartments 14 has a respective one of the sensors 48 associated therewith. Each of the sensors 48 emits a detection signal, and each of the sensors 48 may be magnetic sensors of the like.

The tab 36 on the door 30 that is aligned with the respective compartment 14 is aligned with the sensor 48 in the respective compartment 14 when the door 30 on the respective compartment 14 is closed. The detection signal emitted by the sensor 48 in the respective compartment 14 detects the tab 36 on the respective door 30 when the respective door 30 is closed. In this way the closed input is communicated to the pill box control circuit 44. Moreover, the pill box control circuit 44 receives the open input when the detection signal emitted from any of the sensors 48 does not detect the tab 36 on the respective doors 30.

A plurality of light emitters 50 is each coupled to the pill box 12 and each of the light emitters 50 is positioned within a respective one of the compartments 14 to emit light into the respective compartment 14. The light emitter 50 in the respective compartment 14 is turned on when the door 30 on the respective compartment 14 is opened. Additionally, the light emitter in the respective compartment 14 is turned off when the door 30 on the respective compartment 14 is closed. Each of the light emitters 50 may comprise an LED or the like.

A transmission unit 52 is provided and the transmission unit 52 is removably coupled to the pill box 12. The transmission unit 52 is in electrical communication with the sensing unit 42 when the transmission unit 52 is removably coupled to the pill box 12. Moreover, the transmission unit 52 transmits an alert signal when the sensing unit 42 senses that a respective one of the doors 30 has not been opened at a predetermined time. The transmission unit 52 comprises a housing 54 that has an outer wall 56, and the outer wall 56 has a communication port 58 extending inwardly therein.

A transmission control circuit 60 is positioned in the housing 54 and the transmission control circuit 60 receives an alert signal. The communication port 58 is electrically coupled to the transmission control circuit 60. Additionally, the communication port 58 is selectively placed in electrical communication with a data source 62, such as a personal computer or other electronic data storage device. In this way data can be downloaded into the database in the electronic memory 46 when the transmission unit 52 is removably coupled to the pill box 12.

A pair of plugs 64 is each coupled to the outer wall 56 of the housing 54. Each of the data ports 28 in the peripheral wall of the pill box 12 insertably receives a respective one of the plugs 64 when the transmission unit 52 is removably coupled to the pill box 12. Each of the plugs 64 is electrically coupled to the respective data port 28 when the data ports 28 receive the plugs 64. In this way the transmission control circuit 60 is in electrical communication with the pill box control circuit 44. Moreover, the transmission control circuit 60 receives the alert signal when the pill box control circuit 44 does not receive the open input for a respective one of the compartments 14 at the predetermined time stored in the electronic memory 46.

A transceiver 66 is positioned in the housing 54 and the transceiver 66 is electrically coupled to the transmission control circuit 60. The transceiver 66 broadcasts an alarm signal when the transmission control circuit 60 receives the alert signal. The transceiver 66 may be a radio frequency transceiver 66 or the like. A speaker 68 is coupled to the outer wall 56 of the housing 54 to emit an audible alarm outwardly therefrom when the speaker 68 is turned on. The speaker 68 is electrically coupled to the transmission control circuit 60. Additionally, the speaker 68 is turned on when the transmission control circuit 60 receives the alert input to audibly alert a user to take the pills 16 in one of the compartments 14.

A display 70 is coupled to the outer wall 56 of the housing 54 and the display 70 is visible to the user. The display 70 is electrically coupled to the transmission control circuit 60 and the display 70 displays indicia comprising words and symbols for communicating times and dates for taking the pills 16. Additionally, the indicia include numbers for a digital clock. The display 70 may be an LCD or any other type of electronic display. An indicator light 72 is coupled to the outer wall 56 of the housing 54 and the indicator light 72 is electrically coupled to the transmission control circuit 60. The indicator light 72 is turned on to emit light when the transmission control circuit 60 receives the alert input to visibly alert the user to take the pills 16 in one of the compartments 14. A power supply 74 is positioned in the housing 54 and the power supply 74 is electrically coupled to the transmission control circuit 60. The power supply 74 comprises at least one battery.

A bracelet 76 is provided that can be worn on a wrist of the user and the bracelet 76 is in remote communication with the transmission unit 52. The bracelet 76 vibrates when the transmission unit 52 broadcasts the alert signal to alert the user to take the pills 16 in one of the compartments 14 in the pill box 12. The bracelet 76 includes a bracelet control circuit 78 that is coupled to the bracelet 76, and the bracelet control circuit 78 receives a vibrate input. A receiver 80 is coupled to the bracelet 76, the receiver 80 is in wireless electrical communication with the transceiver 66 and the receiver 80 receives the alert signal from the transceiver 66. Moreover, the bracelet control circuit 78 receives the alarm input when the receiver 80 receives the alert signal. The receiver 80 may be a radio frequency receiver or the like.

A vibration unit 82 is provided and the vibration unit 82 is integrated into the bracelet 76. The vibration unit 82 physically engages the bracelet 76 such that the vibration unit 82 vibrates the bracelet 76 when the vibration unit 82 is turned on. Additionally, the vibration unit 82 is turned on when the bracelet control circuit 78 receives the alarm input. In this way the vibration unit 82 to physically alerts the user to take the pills 16 in one of the compartments 14. The vibration unit 82 may be an electronic vibration unit that involves an oscillating, offset wheel or other electro-mechanical vibration mechanism.

A display 84 is coupled to the bracelet 76 and the display 84 on the bracelet 76 is electrically coupled to the bracelet control circuit 78. The display 84 on the bracelet 76 displays indicia and the display 84 on the bracelet 76 may comprise an LCD or the like. A bracelet power supply 86 is positioned in the bracelet 76, the bracelet power supply 86 is electrically coupled to the bracelet control circuit 78 and the bracelet power supply 86 comprises at least one battery.

A personal electronic device 88, such as a smart phone or the like, is included that can be carried by the user. The personal electronic device 88 is in remote communication with the transmission unit 52. Thus, the personal electronic device 88 can alert the user when the transmission unit 52 transmits the alert signal.

In use, the pills 16 are positioned in respective ones of the compartments 14 according to a predetermined prescription and a predetermined dosage schedule. The predetermined prescription and the predetermined dosage schedule are stored in the electronic memory 46 in the pill box 12. The speaker 68 emits the audible alarm and the bracelet 76 vibrates when a respective one of the doors 30 is not opened according to the predetermined dosage schedule. Thus, the user is reminded to take the pills 16 in the compartment 14 corresponding to the respective door 30. In this way the user is reminded when the user forgets to take the pills 16 in any of the compartments 14 in accordance with the predetermined prescription.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A programmable pill box assembly being configured to emit an audible reminder for taking medication, said assembly comprising:
a pill box having a plurality of compartments therein wherein each of said compartments is configured to have pills positioned therein, said plurality of compartments including a first bank of compartments and a second bank of compartments;
a plurality of doors, each of said doors being hingedly coupled to said pill box, each of said doors being aligned with a respective one of said first and second banks of compartments for opening and closing said respective first and second banks of compartments, each of said doors having a tab extending downwardly therefrom;
a sensing unit being coupled to said pill box, said sensing unit being in operational communication with each of said doors such that said sensing unit senses when each of said doors is opened or closed, said sensing unit comprising
a pill box control circuit being coupled to said pill box, said pill box control circuit receiving an open input and a closed input, said pill box control circuit including an electronic memory, said electronic memory storing a database comprising a unique identity assigned to each of said compartments in said pill box, said database further comprising a predetermined schedule for taking the pills in each of said compartments,
a plurality of sensors, each of said sensors being coupled to said pill box, each of said sensors being positioned in a respective one of said compartments, each of said sensors being electrically coupled to said pill box control circuit, said unique identity assigned to each of said compartments having a respective one of said sensors being associated therewith, wherein each of said sensors emits a detection signal, said tab on said door being aligned with said respective compartment being aligned with said sensor in said respective compartment when said door on said respective compartment is closed, said detection signal emitted by said sensor in said compartment detecting said tab on said respective door when said respective door is closed thereby communicating said closed input to said pill box control circuit, said pill box control circuit receiving said open input when said detection signal emitted from any of said sensors does not detect said tab on said respective door;
a transmission unit being removably coupled to said pill box, said transmission unit being in electrical communication with said sensing unit when said transmission unit is removably coupled to said pill box, said transmission unit transmitting an alert signal when said sensing unit senses that a respective one of said doors has not been opened at a predetermined time;
a bracelet being worn on a wrist of the user, said bracelet being in remote communication with said transmission unit, said bracelet vibrating when said transmission unit broadcasts said alert signal wherein said bracelet is configured to alert the user to take the pills in one of said compartments in said pill box; and
a personal electronic device being carried by the user, said personal electronic device being in remote communication with said transmission unit, said personal electronic device alerting the user when said transmission unit transmits said alert signal.

2. The assembly according to claim 1, wherein said pill box has a perimeter wall and a top wall, said top wall having a plurality of openings each being aligned with a respective one of said first and second banks of compartments, said perimeter wall having a pair of data ports extending inwardly therein.

3. The assembly according to claim 2, wherein:
each of said doors has a back edge and a front edge, said back edge of each of said doors being hingedly coupled to said top wall of said pill box;
said tab on each of said doors being aligned with said front edge of said doors, each of said tabs being comprised of an electrically conductive material; and
said plurality of doors including a set of first doors each being aligned with a respective one of said first bank of compartments, said plurality of doors including a set of second doors each being aligned with a respective one of said second bank of compartments, said back edge of each of said set of first and second doors being directed toward a center of said pill box.

4. The assembly according to claim 1, further comprising a plurality of light emitters, each of said light emitters being coupled to said pill box, each of said light emitters being positioned within a respective one of said compartments wherein each of said light emitters is configured to emit light into said respective compartment, each of said light emitters being electrically coupled to said pill box control circuit, said light emitter in said respective compartment being turned on when said door on said respective compartment is opened, said light emitter in said respective compartment being turned off when said door on said respective compartment is closed.

5. The assembly according to claim 2, wherein said transmission unit comprises:
- a housing having an outer wall, said outer wall having a communication port extending inwardly therein;
- a transmission control circuit being positioned in said housing, said transmission control circuit receiving an alert signal, said transmission control circuit having said communication port being electrically coupled thereto, said communication port being selectively placed in electrical communication with a data source thereby facilitating data to be downloaded into said database in said electronic memory when said transmission unit is removably coupled to said pill box; and
- a pair of plugs, each of said plugs being coupled to said outer wall of said housing, each of said data ports in said peripheral wall of said pill box insertably receiving a respective one of said plugs when said transmission unit is removably coupled to said pill box, each of said plugs being electrically coupled to said respective data port when said data ports receive said plugs such that said transmission control circuit is in electrical communication with said pill box control circuit, said transmission control circuit receiving said alert signal when said pill box control circuit does not receive said open input for a respective one of said compartments at the predetermined time stored in said electronic memory.

6. The assembly according to claim 5, wherein said transmission unit comprises a transceiver being positioned in said housing, said transceiver being electrically coupled to said transmission control circuit, said transceiver broadcasting an alarm signal when said transmission control circuit receives said alert signal.

7. The assembly according to claim 6, wherein said transmission unit comprises:
- a speaker being coupled to said outer wall of said housing to emit an audible alarm outwardly therefrom when said speaker is turned on, said speaker being electrically coupled to said transmission control circuit, said speaker being turned on when said transmission control circuit receives said alert input wherein said speaker is configured to audibly alert a user to take the pills in one of said compartments;
- a display being coupled to said outer wall of said housing wherein said display is configured to be visible to the user, said display being electrically coupled to said transmission control circuit, said display displaying indicia comprising words and symbols for communication times and dates for taking the pills;
- an indicator light being coupled to said outer wall of said housing, said indicator light being electrically coupled to said transmission control circuit, said indicator light being turned on to emit light when said transmission control circuit receives said alert input wherein said indicator light is configured to visibly alert the user to take the pills in one of said compartments; and
- a power supply being positioned in said housing, said power supply being electrically coupled to said transmission control circuit, said power supply comprising at least one battery.

8. The assembly according to claim 6, wherein said bracelet includes:
- a bracelet control circuit being coupled to said bracelet, said bracelet control circuit receiving a vibrate input; and
- a receiver being coupled to said bracelet, said receiver being in wireless electrical communication with said transceiver, said receiver receiving said alert signal from said transceiver, said bracelet control circuit receiving said alarm input when said receiver receives said alert signal.

9. The assembly according to claim 8, further comprising:
- a vibration unit being integrated into said bracelet, said vibration unit physically engaging said bracelet such that said vibration unit vibrates said bracelet when said vibration unit is turned on, said vibration unit being turned on when said bracelet control circuit receives said alarm input wherein said vibration unit is configured to physically alert the user to take the pills in one of said compartments;
- a display being coupled to said bracelet, said display on said bracelet being electrically coupled to said bracelet control circuit, said display on said bracelet displaying indicia; and
- a bracelet power supply being positioned in said bracelet, said bracelet power supply being electrically coupled to said bracelet control circuit, said bracelet power supply comprising at least one battery.

10. A programmable pill box assembly being configured to emit an audible reminder for taking medication, said assembly comprising:
- a pill box having a plurality of compartments therein wherein each of said compartments is configured to have pills positioned therein, said plurality of compartments including a first bank of compartments and a second bank of compartments, said pill box having a perimeter wall and a top wall, said top wall having a plurality of openings each being aligned with a respective one of said first and second banks of compartments, said perimeter wall having a pair of data ports extending inwardly therein;
- a plurality of doors, each of said doors being hingedly coupled to said pill box, each of said doors being aligned with a respective one of said first and second banks of compartments for opening and closing said respective first and second banks of compartments, each of said doors having a back edge and a front edge, said back edge of each of said doors being hingedly coupled to said top wall of said pill box, each of said doors having a tab extending downwardly therefrom, said tab on each of said doors being aligned with said front edge of said doors, each of said tabs being comprised of an electrically conductive material, said plurality of doors including a set of first doors each being aligned with a respective one of said first bank of compartments, said plurality of doors including a set of second doors each being aligned with a respective one of said second bank of compartments, said back edge of each of said set of first and second doors being directed toward a center of said pill box;

a sensing unit being coupled to said pill box, said sensing unit being in operational communication with each of said doors such that said sensing unit senses when each of said doors is opened or closed, said sensing unit comprising:
  a pill box control circuit being coupled to said pill box, said pill box control circuit receiving an open input and a closed input, said pill box control circuit including an electronic memory, said electronic memory storing a database comprising a unique identity assigned to each of said compartments in said pill box, said database further comprising a predetermined schedule for taking the pills in each of said compartments; and
  a plurality of sensors, each of said sensors being coupled to said pill box, each of said sensors being positioned in a respective one of said compartments, each of said sensors being electrically coupled to said pill box control circuit, said unique identity assigned to each of said compartments having a respective one of said sensors being associated therewith, each of said sensors emitting a detection signal, said tab on said door being aligned with said respective compartment being aligned with said sensor in said respective compartment when said door on said respective compartment is closed, said detection signal emitted by said sensor in said compartment detecting said tab on said respective door when said respective door is closed thereby communicating said closed input to said pill box control circuit, said pill box control circuit receiving said open input when said detection signal emitted from any of said sensors does not detect said tab on said respective door;
a plurality of light emitters, each of said light emitters being coupled to said pill box, each of said light emitters being positioned within a respective one of said compartments wherein each of said light emitters is configured to emit light into said respective compartment, said light emitter in said respective compartment being turned on when said door on said respective compartment is opened, said light emitter in said respective compartment being turned off when said door on said respective compartment is closed;
a transmission unit being removably coupled to said pill box, said transmission unit being in electrical communication with said sensing unit when said transmission unit is removably coupled to said pill box, said transmission unit transmitting an alert signal when said sensing unit senses that a respective one of said doors has not been opened at a predetermined time, said transmission unit comprising:
  a housing having an outer wall, said outer wall having a communication port extending inwardly therein;
  a transmission control circuit being positioned in said housing, said transmission unit receiving an alert signal, said transmission control circuit having said communication port being electrically coupled thereto, said communication port being selectively placed in electrical communication with a data source thereby facilitating data to be downloaded into said database in said electronic memory when said transmission unit is removably coupled to said pill box;
  a pair of plugs, each of said plugs being coupled to said outer wall of said housing, each of said data ports in said peripheral wall of said pill box insertably receiving a respective one of said plugs when said transmission unit is removably coupled to said pill box, each of said plugs being electrically coupled to said respective data port when said data ports receive said plugs such that said transmission control circuit is in electrical communication with said pill box control circuit, said transmission control circuit receiving said alert signal when said pill box control circuit does not receive said open input for a respective one of said compartments at the predetermined time stored in said electronic memory;
  a transceiver being positioned in said housing, said transceiver being electrically coupled to said transmission control circuit, said transceiver broadcasting an alarm signal when said transmission control circuit receives said alert signal;
  a speaker being coupled to said outer wall of said housing to emit an audible alarm outwardly therefrom when said speaker is turned on, said speaker being electrically coupled to said transmission control circuit, said speaker being turned on when said transmission control circuit receives said alert input wherein said speaker is configured to audibly alert a user to take the pills in one of said compartments;
  a display being coupled to said outer wall of said housing wherein said display is configured to be visible to the user, said display being electrically coupled to said transmission control circuit, said display displaying indicia comprising words and symbols for communication times and dates for taking the pills;
  an indicator light being coupled to said outer wall of said housing, said indicator light being electrically coupled to said transmission control circuit, said indicator light being turned on to emit light when said transmission control circuit receives said alert input wherein said indicator light is configured to visibly alert the user to take the pills in one of said compartments; and
  a power supply being positioned in said housing, said power supply being electrically coupled to said transmission control circuit, said power supply comprising at least one battery;
a bracelet being worn on a wrist of the user, said bracelet being in remote communication with said transmission unit, said bracelet vibrating when said transmission unit broadcasts said alert signal wherein said bracelet is configured to alert the user to take the pills in one of said compartments in said pill box, said bracelet including:
  a bracelet control circuit being coupled to said bracelet, said bracelet control circuit receiving a vibrate input;
  a receiver being coupled to said bracelet, said receiver being in wireless electrical communication with said transceiver, said receiver receiving said alert signal from said transceiver, said bracelet control circuit receiving said alarm input when said receiver receives said alert signal;
  a vibrating unit being integrated into said bracelet, said vibration unit physically engaging said bracelet such that said vibration unit vibrates said bracelet when said vibration unit is turned on, said vibration unit being turned on when said bracelet control circuit receives said alarm input wherein said vibration unit is configured to physically alert the user to take the pills in one of said compartments;

a display being coupled to said bracelet, said display on said bracelet being electrically coupled to said bracelet control circuit, said display on said bracelet displaying indicia; and a bracelet power supply being positioned in said bracelet, said bracelet power supply being electrically coupled to said bracelet control circuit, said bracelet power supply comprising at least one battery; and a personal electronic device being carried by the user, said personal electronic device being in remote communication with said transmission unit, said personal electronic device alerting the user when said transmission unit transmits said alert signal.

\* \* \* \* \*